(12) United States Patent
Sharp (10) Patent No.: US 6,283,909 B1
(45) Date of Patent: Sep. 4, 2001

(54) CONTAINER FOR SUPPLYING MEDICAL PRODUCTS AND DISPOSAL OF MEDICAL WASTE MATERIAL

(76) Inventor: Fraser R. Sharp, 1830 Greer Ave., Vancouver, B.C. (CA)

( * ) Notice: Subject to any disclaimer, the term of this patent is extended or adjusted under 35 U.S.C. 154(b) by 0 days.

(21) Appl. No.: 09/235,280

(22) Filed: Jan. 22, 1999

(51) Int. Cl.$^7$ .................................................. A61J 1/00
(52) U.S. Cl. ....................... 588/258; 220/908; 206/366; 588/900
(58) Field of Search .................... 220/908, 817, 220/819, 255, 826, 811, 812, 345.2, 256, 259; 206/366, 370; 588/249, 900

(56) References Cited

U.S. PATENT DOCUMENTS

| | | | |
|---|---|---|---|
| 4,121,755 | * 10/1978 | Meseke et al. | 206/366 |
| 4,315,592 | * 2/1982 | Smith | 206/366 |
| 4,779,728 | * 10/1988 | Hanifl et al. | 206/366 |
| 4,842,138 | * 6/1989 | Sandel et al. | 206/370 |
| 4,890,733 | * 1/1990 | Anderson | 206/366 |
| 4,955,477 | * 9/1990 | Bruno | 206/366 |
| 4,969,554 | 11/1990 | Sawaya . | |
| 5,076,429 | * 12/1991 | Patrick et al. | 206/366 |
| 5,080,251 | 1/1992 | Noack . | |
| 5,176,256 | 1/1993 | Sawaya . | |
| 5,193,740 | * 3/1993 | Newborough et al. | 206/370 |
| 5,240,176 | * 8/1993 | Akers | 206/366 |
| 5,259,503 | 11/1993 | Steingraber, Jr. . | |
| 5,387,735 | 2/1995 | Ponsi . | |
| 5,474,180 | 12/1995 | Robinson et al. . | |
| 5,494,186 | * 2/1996 | Marsh | 206/366 |
| 5,570,783 | 11/1996 | Thorne et al. . | |
| 5,630,506 | 5/1997 | Thorne et al. . | |
| 5,848,692 | 12/1998 | Thorne et al. . | |
| 5,947,285 | * 9/1999 | Gaba et al. | 206/370 |
| 5,967,317 | * 10/1999 | Wright | 206/370 |

FOREIGN PATENT DOCUMENTS

| | | |
|---|---|---|
| 0541339 | 5/1993 | (EP) . |
| 2294036 | 4/1996 | (GB) . |

* cited by examiner

*Primary Examiner*—David Bagnell
*Assistant Examiner*—Frederick L. Lagman
(74) *Attorney, Agent, or Firm*—Nixon & Vanderhye (57) ABSTRACT

A medical supply and sharps container includes a container body having a cover. Medical apparatus may be supplied the user in the container. The cover includes a lid or door defining an entry slot into the container after the medical apparatus has been removed and the container has been converted to a sharps container. In one form, a lid defines an entry slot through the cover for disposition of medical waste material onto an inclined chute underlying the lid whereby an individual's hand or fingers cannot be passed through the entry slot into the container. In another form, a hood and balanced shelf arrangement is releasably secured to the cover in a manner to open a door overlying an opening through the cover upon securement of the arrangement to the cover and to close the door upon removal of the arrangement from the cover.

33 Claims, 8 Drawing Sheets

CONTAINER FOR SUPPLYING MEDICAL PRODUCTS AND DISPOSAL OF MEDICAL WASTE MATERIAL

TECHNICAL FIELD

The present invention relates generally to handling of medical products and particularly relates to a container for supplying medical products such as syringes and disposing of waste medical materials such as used syringes and needles.

BACKGROUND

Disposal of medical waste material is an ever-present and on-going problem for medical practitioners and facilities such as hospitals and doctors' offices. Typically, medical waste material such as used syringes with projecting, sometimes exposed needles, swabs, bandages, gauze, gloves and the like are placed in what is known as a sharps container. These sharps containers allow disposal of dangerous material such as used needles but additionally prevent retrieval of same by a restrictive opening used for depositing the contaminated materials. The sharps container is typically formed of a plastic, metal or sometimes a corrugated fiberboard material having the restricted opening for receiving the waste material. Use of fiberboard sharps containers is a cost-effective solution to the problem of medical waste disposal because the cost of fiberboard containers is very substantially less than the cost of metal or plastic-type containers and fiberboard containers are substantially equally effective.

While transmission of diseases such as hepatitis or HIV is not solely limited to handling and disposal of medical waste material, substantial disease transmission to medical, as well as non-medical, for example, housekeeping personnel, can and does occur during usage and improper disposal or handling of needles or sharps containers. For example, housekeeping personnel, untrained, or even when trained, in handling medical waste, may inadvertently incur a needle-stick injury while attempting to discard used syringes which have not otherwise been properly disposed. Also, the supply of disposable medical products in containers such as boxes which are discarded once the products are removed and the provision of additional sharps containers for disposal of the used medical products results in the use of two or more containers for handling essentially the same product. Consequently, there is a demonstrated need for a single container which will provide both functions, supply of product and disposal after use.

DISCLOSURE OF THE INVENTION

In accordance with an embodiment of the present invention, there is provided a container having a plurality of walls including side and bottom walls defining a container body and a cover which can be selectively secured to close the container when the container is used for disposal of medical waste products. The container body is preferably formed of fiberboard, i.e., corrugated cardboard material, and includes at least one either interior or exterior waterproof liner along the sides and bottom of the container body. The cover, however, is preferably formed of a rigid transparent or semi-transparent plastic material whereby the contents of the container body can be viewed through the cover.

In one aspect of the present invention, the container body and cover may comprise the container in which the disposable medical products are supplied for use. For example, the container may be filled and shipped with disposable syringes enclosed within packages providing internal syringe sterility as usual. Thus, the cover may be suitably secured to the container body during shipping and handling until such time as the products therein are ready for use. The products can then be emptied from the container whereby the container can be transformed into a sharps container. Alternatively, the medical products may be supplied from the container with another previously supplied, but empty, container serving as a sharps container.

To transform the supply container into a sharps container, the cover in one aspect of the present invention has an articulated pivoted lid which normally closes an opening in the cover when used as part of a container for supplying medical products. The lid also includes a chute or ramp inclined from one edge of the opening into the interior of the container. The chute or ramp can be rigidly secured in its inclined position or displaced from the plane of the cover into an inclined position after the lid has been pivoted to define the access opening through the cover onto the ramp. The lid is articulated such that the extent of the opening between the free edge of the lid and the margin of the opening in the cover, i.e., the container entry slot, is limited to prevent a user from inserting his hand through that opening and into the sharps container. The chute or ramp may further limit access if retrieval is attempted. With the lid pivoted outwardly and the ramp in position, the cover can be secured to the container body, preferably by bonding. For example, the container may have flanges directed inwardly from its side and end walls and have a permanent adhesive on the outer surface of the flanges covered by a release paper. The upper end edges of the sides forming part of the flanges provide sufficient resistance to secure the cover to the container body, the adhesively covered flanges providing for additional securement. By removing the release paper and adhering the cover to the flanges, the cover may be permanently attached to the container body. The sharps container is thus ready for use and medical waste material can be inserted through the opening onto the ramp or chute for disposition within the container body. With the container body being lined, either exteriorly or interiorly or both, with a waterproof material in addition to a puncture-resistant double layer of corrugated fiberboard, the waste material including, for example, syringes with exposed needles, may be disposed out of harm's way. When the container is filled to capacity, for example, three-quarters full, the articulated lid is pivoted to close the opening. Tabs provided on the lid lock the lid in place on the cover. The sharps container may then be disposed of in the normal fashion, i.e., the bottom end and sides being leakproof and puncture-resistant and the top being irreversibly closable.

In another form of the present invention, the lid and ramp cooperate one with the other such that any attempt to increase the size of the entry opening into the container by further pivoting the lid outwardly relative to the cover causes the ramp or chute to close the entry opening in the cover. To accomplish this, an arm depends from opposite sides of the lid adjacent its pivot axis and engages below the free end of the ramp. As the lid is pivoted into a further open position, the ends of the arms raise the ramp to a position closing the opening. In this manner, an individual's hands cannot be disposed through the entry opening into the sharps container.

In a further form of the present invention, the cover of the supplied container is modified to a configuration for use with the hood and pivoted shelf arrangement of a standard sharps container, the latter, in turn, being modified for use with the cover hereof. Standard sharps containers have a cover with an integral arcuate hood defining an entry opening into the container. Disposed in that entry opening is a pivoted shelf. When medical waste material is disposed on the shelf, the shelf pivots in a direction to drop the material into the container. These hood and pivoted shelf arrangements typically integrated into the covers of the sharps containers are expensive to manufacture and are disposed of each time with the container when the container becomes full of medical waste material. In accordance with an aspect of the present invention, a modified configuration of a hood and pivoted shelf arrangement is releasably or permanently secured to the cover of the medical supply container when adapted as a sharps container. Particularly, the cover is provided with an opening having a sliding articulated or non-articulated door movable between open and closed positions. Rails are formed along either the underside or topside of the cover, enabling sliding movement of the door between open and closed positions. Rails are also provided along an outer surface of the cover on opposite sides of the opening. The hood and pivoted shelf arrangement hereof has laterally directed flanges cooperable with the rails whereby the hood and pivoted shelf arrangement are slidable along the rails to overlie the opening in the cover.

One of the walls of the hood also has a detenting arrangement which is cooperable with the door such that when the hood and pivoted shelf arrangement is engaged in the outer rails, the detent on the hood end wall engages a corresponding element on the door. Upon sliding the hood and pivoting shelf arrangement into overlying relation relative to the opening, the door is likewise displaced into its open position by the sliding movement of the hood. In this manner, access into the interior of the sharps container is provided by the pivoted shelf and hood arrangement. When the sharps container is full, the hood may be removed from the cover by sliding the hood and pivoted shelf arrangement from the cover along the rails. With that sliding action, the detent draws the door into a position closing the opening. Suitable locking or sealing arrangements can be provided to secure the door in a closed position.

In a preferred embodiment according to the present invention, there is provided a container for hazardous medical waste material comprising a container body including a plurality of walls, a cover for each container body, the cover defining an opening for receiving the waste material for disposition within the container body and having a ramp underlying the opening and extending into the container body for receiving waste material, a lid attached to the cover for movement between first and second positions, the lid in the first position overlying at least a major portion of the opening and having an edge defining with the cover an entry slot of predetermined size adjacent the ramp and through which the waste material is received for movement along the ramp into the container body, the lid being movable from the first position into the second position closing the opening and having at least one element engageable with the container body for securing the lid in the second position closing the container.

In a further preferred embodiment according to the present invention, there is provided a container for supplying medical products and disposing of medical waste material comprising a container body including a plurality of walls for confining a supply of the medical products, a cover for closing the container body when the container body contains the medical products, an adhesive on one of the container body and the cover ineffective to secure the container body and the cover to one another when the container is used for supplying the medical products and effective to secure the container body and the cover to one another when the container is used for disposing medical waste, the cover defining an opening for receiving the waste material when the container is used as a waste material container, the cover including an inclined surface underlying the opening and extending into the container body for receiving waste material, a lid carried by the cover for movement between first and second positions, the lid in the first position restricting a portion of the opening and having an edge defining with the cover an entry slot of predetermined size adjacent the inclined surface through which the waste material is received for sliding movement along the inclined surface into the container body, the lid being movable from the first position into the second position closing the opening and having at least one element engageable with the cover for securing the lid in the second position closing the opening through the cover whereby the medical waste material within the container body is sealed by the cover.

In a still further preferred embodiment according to the present invention, there is provided a container for hazardous medical waste material comprising a container body including a plurality of walls and a cover, the cover defining an opening for receiving the waste material for disposition within the container body, a door attached to the cover for movement between open and closed positions, a hood carried by the cover for movement relative to the cover between a first position out of registration with the opening and a second position in registration with and overlying the opening, the hood and the door being coupled to one another such that the door is movable from the open position to the closed position in response to movement of the hood from the second position to the first position, the hood defining an entry slot of predetermined size through which waste material is received for disposal in the container body.

In a still further preferred embodiment according to the present invention, there is provided a method of converting a medical products supply container to a medical waste materials container comprising the steps of providing a container body having a plurality of walls and a bottom wall and a cover having an opening and a closure member movable between closed and open positions, supplying medical products in the container body, closing the container body with the cover and with the closure member in a closed position, transporting the medical products in the container to a user, removing the medical products from the container body, converting the supply container to a medical waste container including by moving the closure member to an open position and in response thereto providing a restricted entry slot into the container body whereby a user's hand cannot pass through the slot to the opening into the container body and among medical waste materials disposed in the container.

BEST MODE FOR CARRYING OUT THE INVENTION

Figure 1:
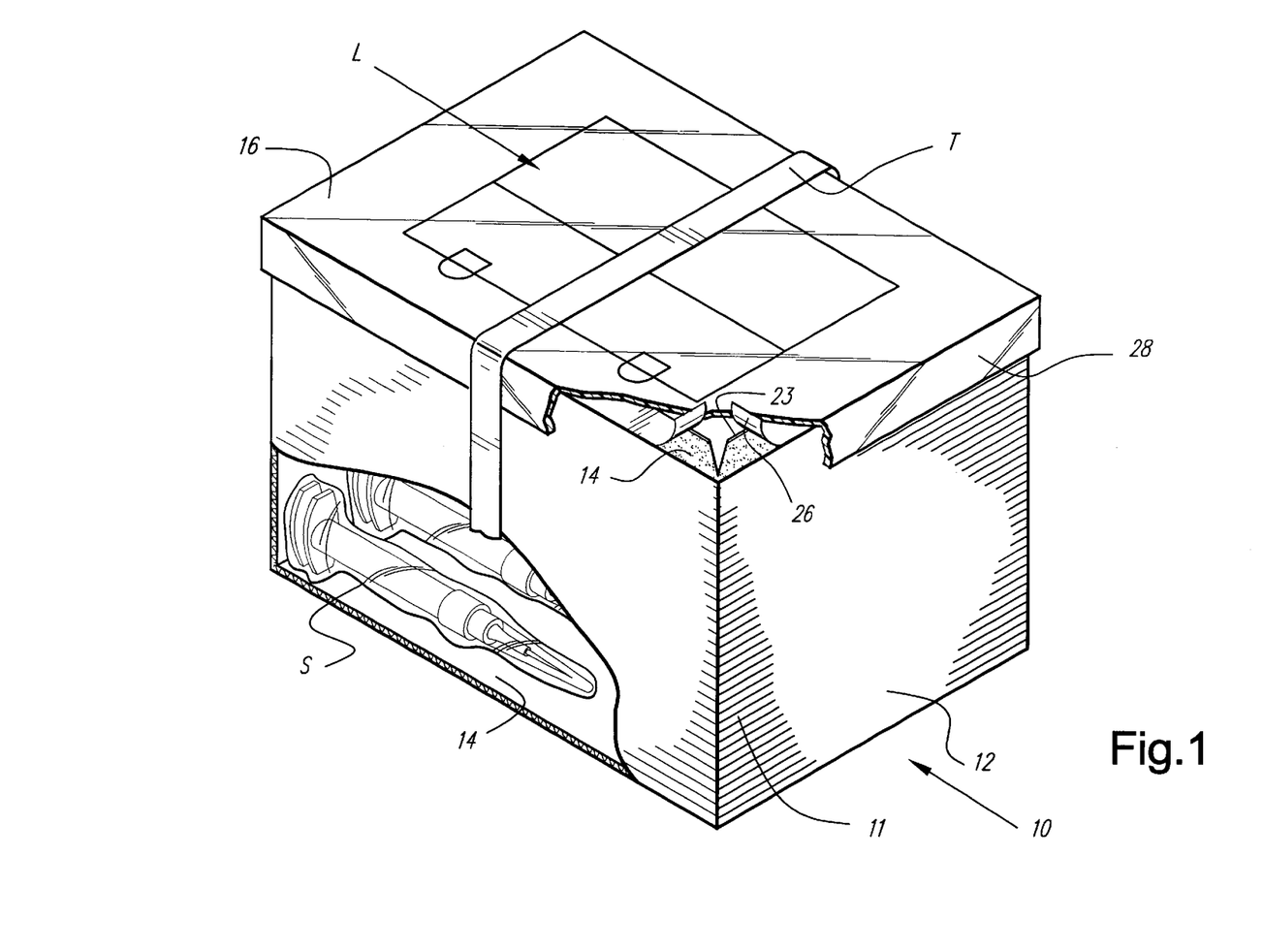
FIG. 1 is a perspective view of a combined medical supply and sharps container with portions broken out illustrating the supply of medical syringes within the container body.
Figure 2:
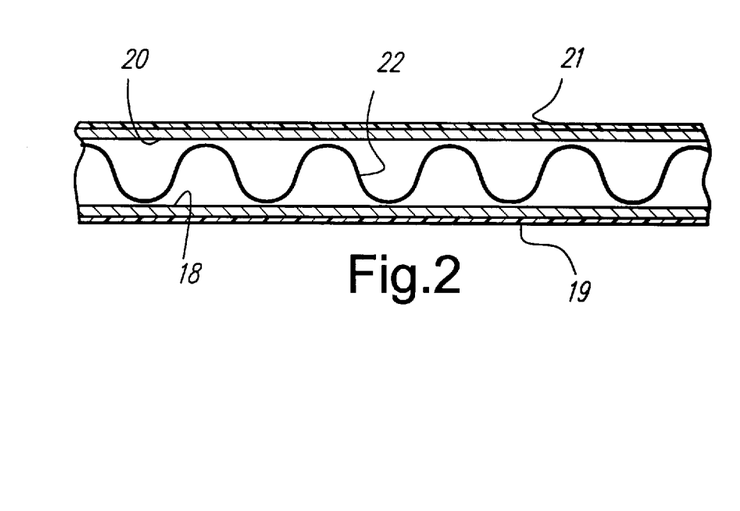
FIG. 2 is a fragmentary enlarged cross-sectional view of a portion of the side or bottom walls of the container body of FIG. 1.

Referring now to the drawings, particularly to FIG. 1, there is illustrated a combined medical apparatus supply and sharps container, generally designated 10, and comprised of a container body 11 having side walls 12, a bottom wall 14 and a cover 16. Container 10 may assume a variety of configurations other than the generally rectangular container illustrated. For example, the container body may be cylindrical in shape, with a correspondingly-shaped cylindrical cover 16, or may have fewer or more sides than the four sides of the standard rectilinear box-like configuration illustrated, with a correspondingly-shaped cover 16. The container is generally leakproof and puncture-resistant. Preferably, the side walls 12 and bottom wall 14 of container 10 are formed of fiberboard. For example, and referring to FIG. 2, the fiberboard may comprise a corrugated cardboard having inner and outer sheets of cardboard materials 18 and 20, respectively, with a corrugated layer 22 between sheets 18 and 20. Waterproof lining material 19 and 21 may be supplied on either the interior or exterior surfaces, respectively, of the side walls and bottom of the container or both such interior or exterior surfaces. For example, such lining material may comprise sheet plastic material or the fiberboard may be treated with waterproofing material, such as a vinyl paint or a plastic coating, such as shrink wrap. Additionally, the fiberboard material may be impregnated with a substance such as iodine which changes color when contacted by liquid. This would indicate that the liquid contents within the container have penetrated the side or bottom walls of the container, indicating a defective sharps container. Other types of hygroscopic substances which provide a color shift, when hydrated, may also be used.

Again referring to FIG. 1, the upper edges of the side walls 12 of container 10 preferably have inwardly horizontally directed flanges 23 with adhesive 24 applied along their upper faces. The adhesive is preferably a pressure-sensitive adhesive and, when the container is provided as a medical apparatus supply container, release paper, such as silicone-coated paper 26 in strip form overlies adhesive 24. The release paper 26 protects the adhesive which, being pressure-sensitive, would otherwise be exposed and contact the margins of the cover 16 prior to adaptation of the container as a sharps container, as explained below.

The cover 16 is preferably formed of a clear or semi-transparent plastic material having depending margins 28 for overlying the upper margins of the side walls 12. It will be appreciated that when the container is used for supplying medical apparatus, the release paper 26 overlies adhesive 24 whereby the cover 16 is not adhered to the flanges 23 of the container body. Consequently, as illustrated in FIG. 1, when container 10 is provided as a medical apparatus supply container, with medical apparatus such as the syringes S disposed within the container, the cover 16 is otherwise suitably retained on the side walls, closing the container. For example, tape T may be provided overlying the cover and side walls to releasably secure the cover to the container, retaining the syringes within the container. Other suitable types of securement will readily suggest themselves.

Figure 3:
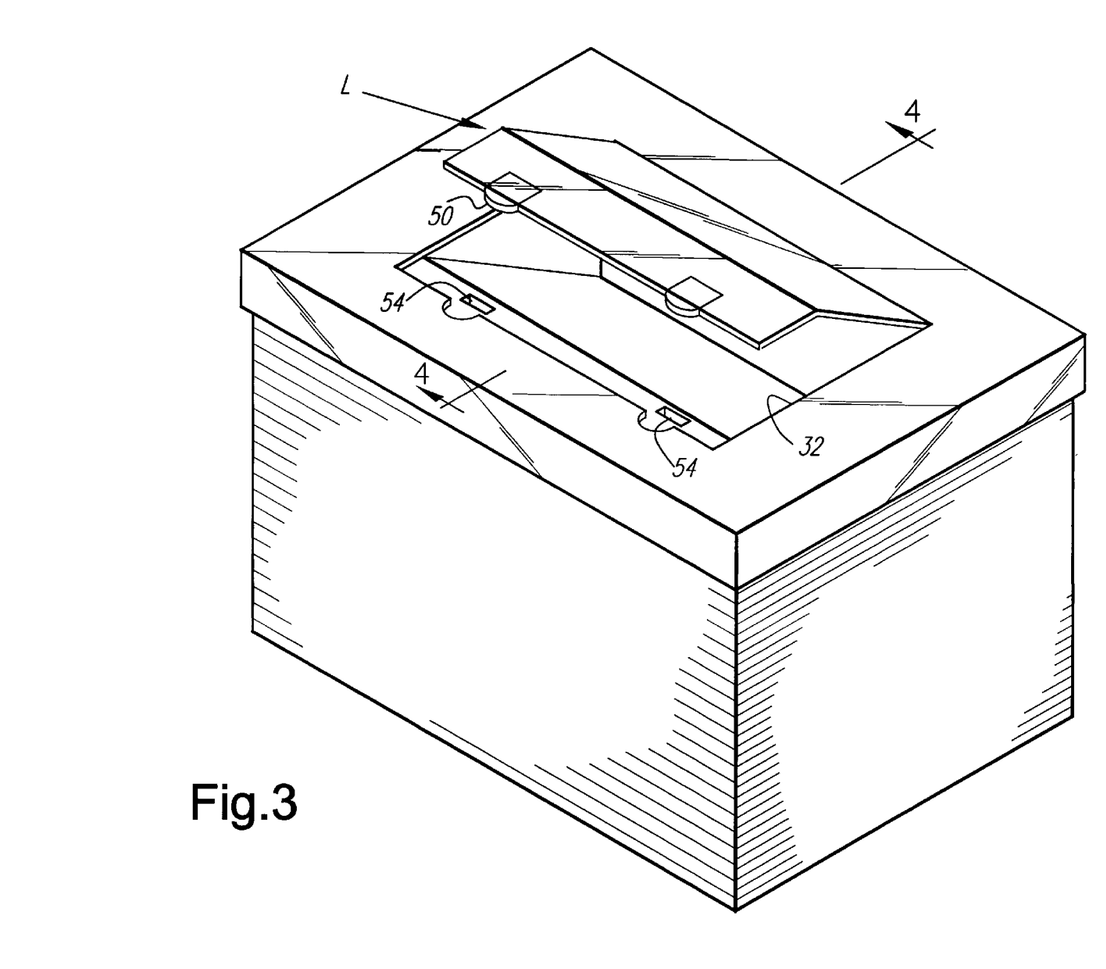
FIG. 3 is a perspective view of the container of FIG. 1 illustrating its use as a sharps container with its lid in an open position.
Figure 4:
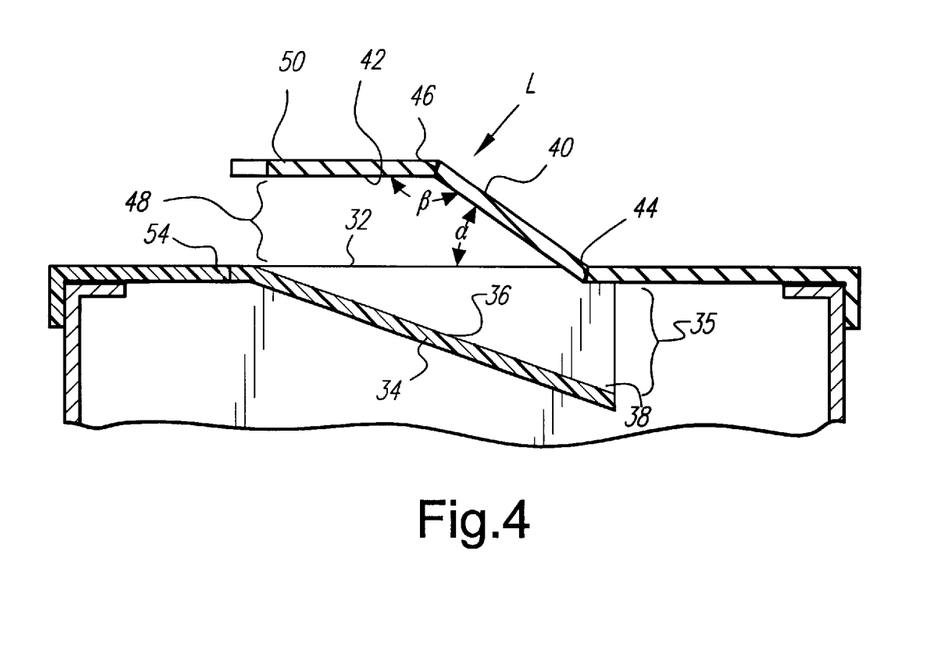
FIG. 4 is a cross-sectional view thereof taken generally about on line 4—4 of FIG. 3.
Figure 5:
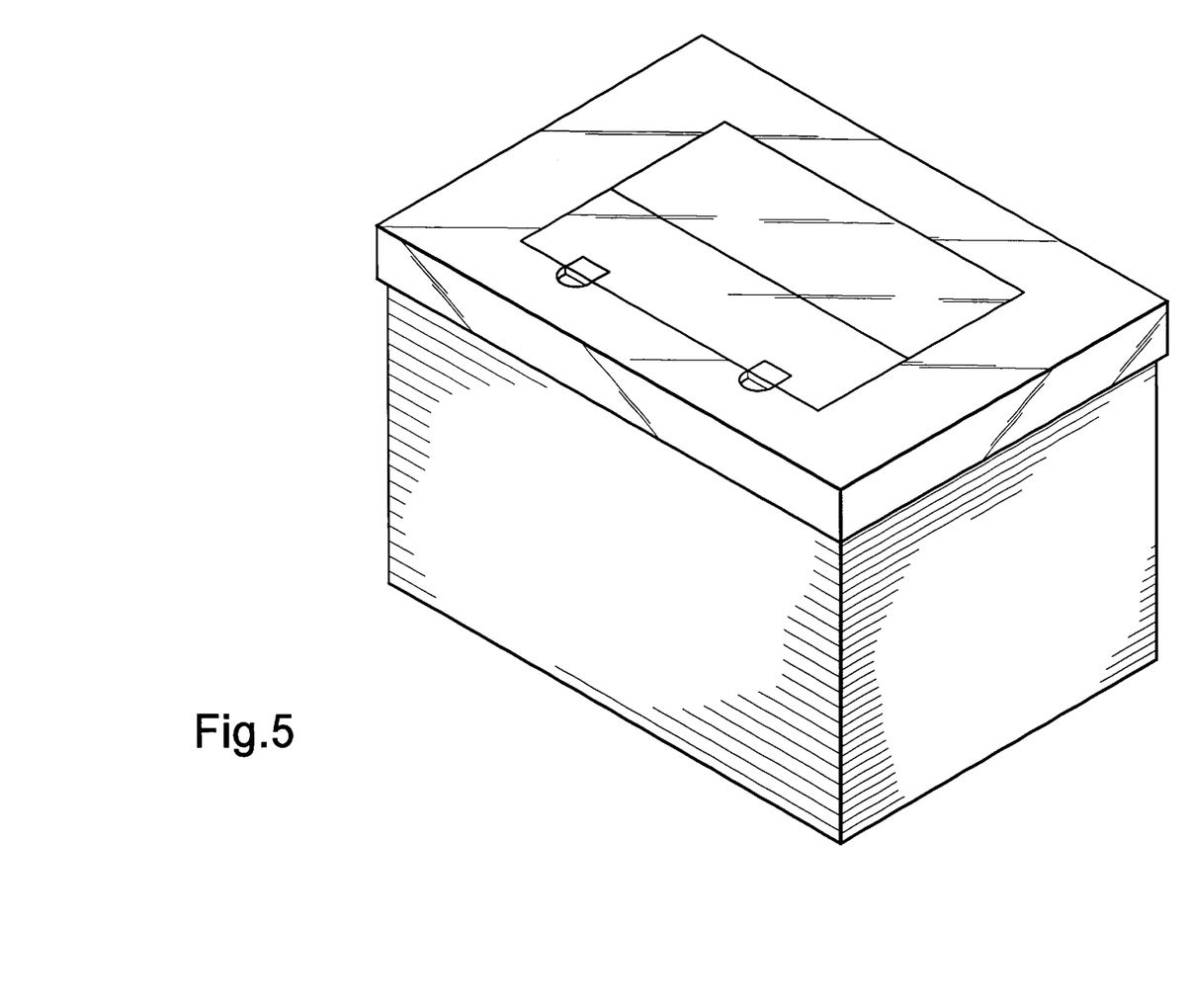
FIG. 5 is a view similar to FIG. 3 with the sharps container filled with medical waste material and illustrated in a closed condition.

To use the container 10 as a sharps container, the cover 16 is provided with a closure member, preferably an integrally formed lid, generally indicated L and best illustrated in FIGS. 3 and 4. Lid L is preferably located centrally of the cover 16 and defines an opening 32 through the cover. Directly below opening 32 and in substantial vertical registration therewith is an inclined chute or ramp 34 having a bottom wall 36 and opposite side walls 38 depending from the underside of cover 16. The ramp 24 terminates in the container body in a free edge defining an aperture 35 with the cover 16. Preferably, the lid is articulated and comprises a pair of flaps 40 and 42 integrally molded with the cover 16. Flap 40 is hinged to the cover at 44, while flap 42 is hinged to flap 40 at 46. These hinges are of a type formed during molding which permit movement only to a very limited extent in one direction. That is, flap 40, for example, is pivoted at hinge 44 to the cover for movement between a first position illustrated in FIG. 4, in which the flap 40 forms an acute angle α with the cover 16 and a second position illustrated in FIG. 5 in which flap 40 (as well as flap 42) lies coplanar with cover 16. Further easy movement of flap 40 away from the cover to enlarge the acute angle α is resisted or precluded by the nature of the hinge 44. Moreover, the hinge 44 is constructed such that there is a bias applied to the flap 40 raising the flap to the first position illustrated, maintaining the lid L in an open position relative to opening 32. Flap 42 is connected to flap 40 at hinge 46. The hinge 46 biases the flap 42 to a predetermined obtuse angle β with flap 40 as illustrated in FIG. 4. Thus, flap 42 is biased to define with the opening 32 an entry slot 48 between the free edge of flap 42 and the edge of opening 32 at the beginning or top of ramp 34. The hinged constructions substantially prevent movement of the flaps in a direction which would enlarge the entry slot 48. The entry slot 48 is thus of a predetermined size, preferably of a size which would inhibit or prevent an individual's hand or fingers from gaining entry into the container body 11 through slot 48.

Figure 3A:
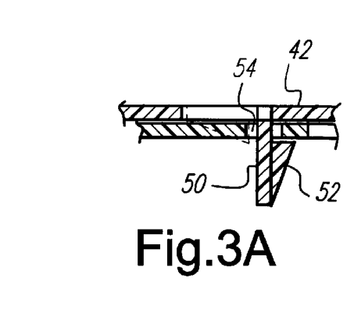
FIG. 3A is a fragmentary enlarged cross-sectional view illustrating a locking mechanism for locking the lid to the container cover.

As illustrated in drawing FIGS. 3 and 3A, the free edge of flap 42 has a pair of projecting tabs 50. Tabs 50 are employed to lock the lid L in a position closing the opening 32 with the flaps 40 and 42 lying substantially in the plane of cover 16. The tabs 50 may be provided with a locking means, for example, one or more teeth 52 may be formed on the underside of the tabs 50. The tabs are pivotal relative to flap 42 and are receivable in locking slots 54 formed along a forward recessed margin of opening 32. When the lid L is disposed coplanar with the cover 16, the tabs 50 may be received in slots 54 and locked in place, securing and sealing the lid in overlying relation to opening 32. It will be appreciated that a wide variety of different types of locking means can be provided for this purpose.

To use the container hereof, and referring to FIG. 1, the medical devices, for example, the syringes S, are packed in the container. In the specific example illustrated, syringes are disposed within individual, preferably plastic, packages to maintain the syringes sterile. Once the container is filled with a supply of syringes, the cover 16 is applied and suitably secured to the container body, for example, by the tape T. When the medical supplies are received by a user, the cover 16 is removed and the contents of the container 10 are emptied into suitable storage areas for subsequent use. The supplied container may then be converted for use as a sharps container. To accomplish this, the release paper 26 is removed from its position overlying adhesive 24 and cover 16 is reapplied to the container body 11. With the release paper removed, the adhesive on flanges 23 contacts the underside of the cover and firmly affixes cover 16 to the container body 11. It will be appreciated that the adhesive and release paper can be applied along the underside of the cover rather than to the flanges 14. Also, by removing the tape T, the lid L will naturally reorient, i.e., raise the flaps 40 and 42 into the position illustrated in FIG. 4. This automatic reorientation of the lid L exposes the entry slot 48 through which waste medical material such as the syringes originally supplied with the container can be inserted for disposal in and with the container 10. For example, the used syringes may be inserted through the entry slot 48 for sliding movement along ramp 34 and through aperture 35 into the container body 11. It will be appreciated that the combination of the ramp 34 and the lid L defining the entry slot 48 prevent intentional or inadvertent movement of an individual's hand or fingers into the container body 11.

Figure 6:
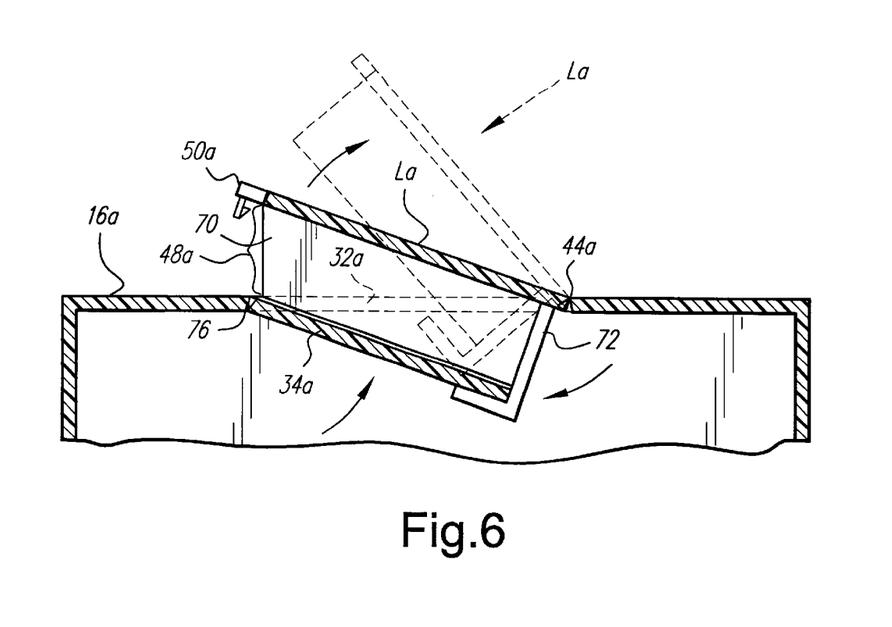
FIG. 6 is a view similar to FIG. 4 illustrating a further form of container cover and lid according to the present invention.

Referring now to the embodiment hereof illustrated in FIG. 6, wherein like reference numerals are applied to like parts followed by the suffix "a," the lid La may comprise a single planar element pivoted to the cover 16a at 44a. In this embodiment, the lid La has a pair of end walls 70 with each end wall 70 carrying a generally L-shaped arm 72 below hinge 44a, arm 72 terminating in a lower flange 74. The arms 72 and flanges 74 lie at opposite ends of the lid La and are spaced one from the other. The chute or ramp 34a in this embodiment is pivoted to the cover at 76, e.g., by a suitable integrally molded plastic hinge, rather than being affixed to the cover as in the prior embodiment. The free end of the chute 34a rests on the flanges 74.

In using this embodiment of the present invention, the cover is secured to the container body as in the prior embodiment by similar-type tabs 50a provided on lid La. After the cover is secured to the container body, the lid La may be pivoted about hinge 44a to the position illustrated whereby an entry slot 48a is provided between the free margin of lid La, the end edges of the walls 70 and the chute 34a adjacent pivot 76. Thus, medical waste material may be disposed through the entry slot 48a onto the chute for disposition in the container body. It will be appreciated that should the lid La be pivoted further upwardly, for example, to the position illustrated by the dashed lines in FIG. 6, the flanges 74 at the ends of the arms 72 will pivot the chute 34a into a generally horizontal position, closing the opening 32a. Hence, any intentional or inadvertent further pivoting movement of the lid La from its illustrated position to further open the entry slot 48a results in movement of the chute 34a toward the closed position.

Figures 7, 7A:
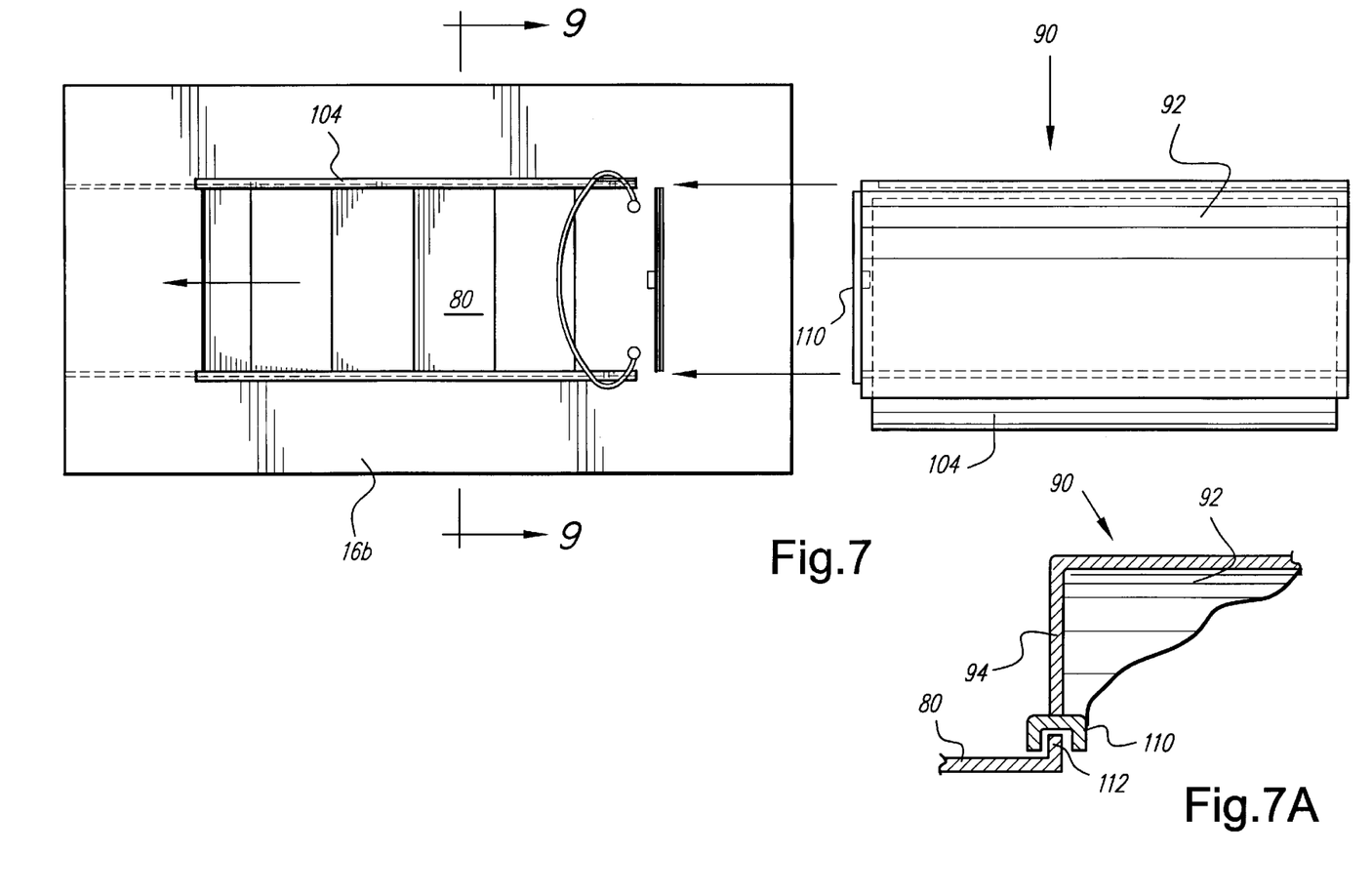
FIG. 7 is a top plan view of a still further form of container according to the present invention employing a hood and pivoted shelf arrangement.
FIG. 7A is a fragmentary cross-sectional view illustrating a connection between the door and the hood and pivoted shelf arrangement.
Figure 8:
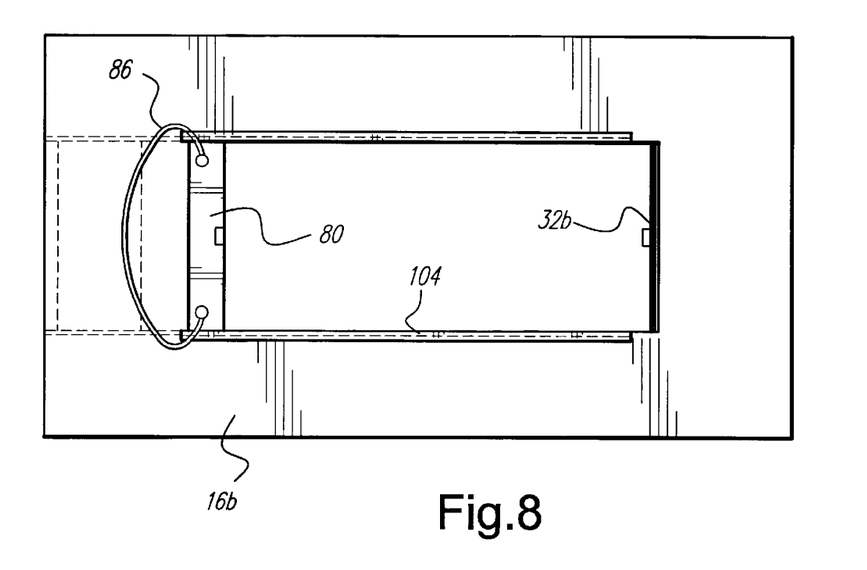
FIG. 8 is a top plan view of the cover with the lid in an open position, the container being useful with or without the hood and shelf arrangement.
Figure 9:
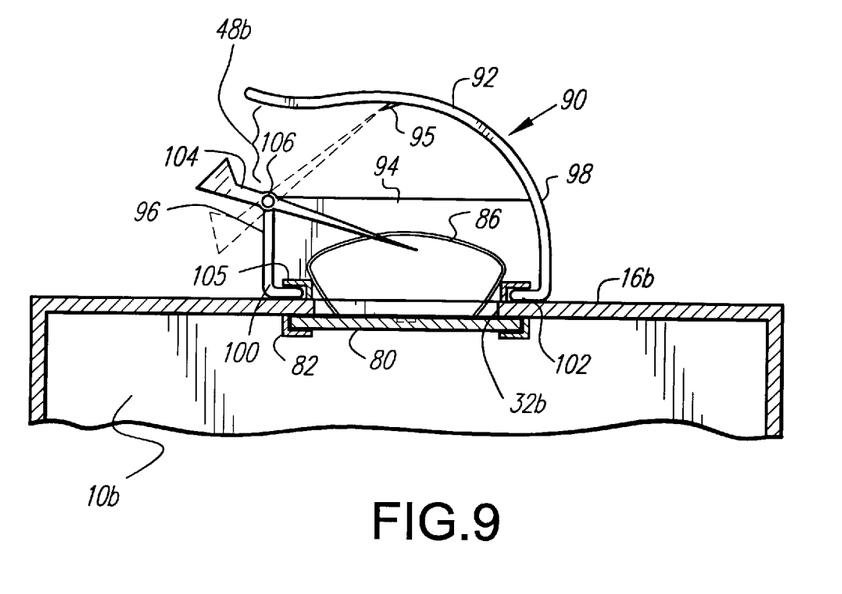
FIG. 9 is a cross-sectional view of the cover taken generally about on line 9—9 in FIG. 7.

Referring now to the embodiment hereof illustrated in FIGS. 7 through 9, wherein like reference numerals are applied to like parts followed by the suffix "b," a closure member, preferably an articulated door 80 is mounted on rails 82 disposed along the underside of the cover 16b adjacent the margins of opening 32b. The side edges of the door 80 ride along the rails 82 and consequently the door 86 is mounted for movement between a closed position illustrated in FIG. 7 and an open position illustrated in FIG. 8. A handle, for example, a plastic loop 86, may be attached to the door whereby the door can be manually displaced between open and closed positions.

Referring particularly to FIG. 9, a hood and balanced shelf arrangement, generally indicated 90, is provided for disposition over the opening 32b. The arrangement 90 includes an arcuate hood 92 overlying a generally rectilinear structure having end walls 94 and side walls 96 and is 98, the latter wall 98 forming part of the upstanding back wall or base of the arcuate hood 92. Hood 92 extends over the upper margins of end walls 94 and side wall 96 to define with the latter an entry slot 48b. The side walls 96 and 98 terminate at their lower ends in inwardly directed flanges 100 and 102, respectively, for engaging along rails 105 formed along the upper surface of the cover 16b and along the edges of the opening 32b. Consequently, the arrangement 90 is slidable along the rails 105 between the position illustrated in FIG. 7 and a position overlying opening 32b. Arrangement 90 also includes a shelf 104 which is pivoted at 106 along the upper margin of the side wall 96. The shelf is balanced about pivot 106. It will be appreciated that the opening between the shelf 104 at the pivot 106 and the free edge of hood 92 defines the entry slot 48b through which medical waste material can be inserted for disposition into container 10b. With the exception of the lower flanges, and the shelf detent described below, the hood 92 and balance shelf 104 are per se known in the sharps container industry. It will be appreciated that waste material disposed on the balance shelf 104 will pivot the shelf downwardly to enable the material to pass into the container through opening 32b. A detent 95 is provided along the underside of the hood 92 for detenting the balance shelf 104 in an elevated position, closing the opening through the arrangement 90. If the hood becomes contaminated, the hood can be disposed of by closing and locking this balance shelf in the elevated position preventing inadvertent discharge of the contaminated waste material.

Referring to FIG. 7A, the arrangement 90 and door 80 are connected to one another when the arrangement 90 is disposed on the cover 16b for opening the door in response to sliding movement of the arrangement 90 into a position overlying opening 32b. To accomplish this, for example, the forward end wall 94 of arrangement 90 has a downwardly opening channel 110 which engages an upstanding flange 112 formed on the free edge of the door 80. With the channel 110 engaged over the flange 112, it will be appreciated that as the arrangement 90 is displaced longitudinally along rails 105 into a position overlying opening 32b, the door 80 is also displaced from its closed position illustrated in FIG. 7 to an open position illustrated in FIG. 8 (the door is illustrated in FIG. 8 without the overlying arrangement 90). Suitable detents, not shown, are provided between the cover and the arrangement 90 such that when the arrangement 90 overlies the opening 32b, the arrangement 90 is releasably locked relative to the cover 16b. It will be appreciated that mechanisms of the channel 110 and flange 112 connection may be used to enable the door to follow the movement of the arrangement 90. For example, detents between the hood and door may be used.

To use the embodiment of the sharps container set forth in FIGS. 7–9, it will be appreciated that the container 10 is supplied with the medical apparatus contained therein as previously described in connection with the embodiments illustrated in FIGS. 1–6. When the contents of the container have been emptied, the cover may be applied to the container body 11b as previously described. It will be appreciated that the hood arrangement 90 is not supplied with the container. Rather, the arrangement 90 is of sturdy, preferably plastic construction, and is retained by the hospital or medical facility for repeated use in connection with the container 10 when the latter is converted for use as a sharps container. Thus, the arrangement 90 is applied to the cover by engaging the channel 110 over the upwardly projecting flange 112 on the cover door 80 and engaging the flanges 100 and 102 along the rails 105. By sliding the arrangement 90 into a position overlying opening 32b, the door 80 is also displaced along rails 82 into a position illustrated in FIG. 10, providing access through opening 32b. With the shelf 104 overlying the access opening 32b, medical waste material disposed on the shelf pivots the shelf under the weight of the material to displace the material into the container body. Once the sharps container is full of medical waste material, the arrangement 90 may be displaced along rails 86 for removal from the cover 16b. With the channel 110 engaging flange 112, it will be appreciated that the door 80 automatically slides along rails 82 to close the opening 32b. Once the opening has been closed, the arrangement 90 can be removed from the cover for reuse with another similar type sharps container and the door can be suitably secured to prevent it from reopening. It will be appreciated that, while the door is disclosed for movement along guide rails formed along the underside of the cover, the door may be disposed along the outside of the cover. Thus, the rails may be provided along the upper surface of the cover along the opening 32b.

Figure 10:
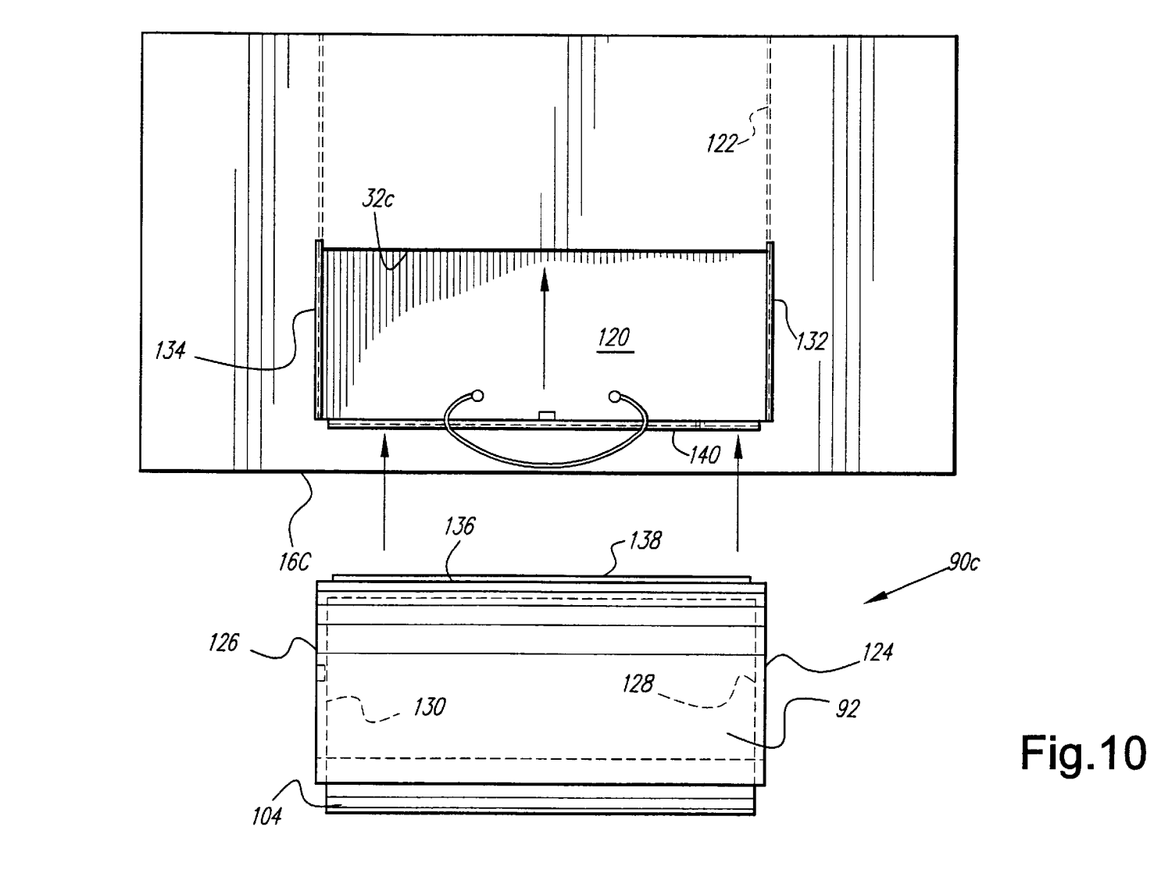
FIG. 10 is a view similar to FIG. 7 illustrating a further form of the invention.

Referring now to FIG. 10, wherein like reference numerals are applied to like parts as in FIG. 7, followed by the suffix "c," there is illustrated a hood and balanced shelf arrangement, generally designated 90c, for disposition over an opening 32c in the cover 16c for the container. As illustrated, the opening 32c is generally rectilinear with its long dimension lying generally parallel to the long dimension of the generally rectangular cover 16c and underlying container, not shown in drawing FIG. 10. The cover includes a door 120 mounted for sliding movement on rails 122 between the illustrated position closing opening 32c and a position offset from opening 32c whereby door 120 is mounted for movement between the closed position illustrated in FIG. 10 and an open position.

The hood and balanced shelf arrangement 90c is constructed similarly as illustrated in FIG. 7, except that it is the end walls 124 and 126 which terminate at their lower ends in inwardly directed flanges 128 and 130, respectively, for engaging along respective rails 132 and 134 formed along the upper surface of cover 16c and the end edges of opening 32c. Consequently, the arrangement 90c is slidable along the rails 132 and 134 between the position illustrated in FIG. 10 and a position overlying opening 32c. Additionally, the forward side wall 136 of arrangement 90c has a downwardly opening channel 138 similar to channel 110 of the prior embodiment which engages an upstanding flange 140 formed on the free edge of door 120. With the channel 138 engaged over the flange 140, the door 120 is displaced from its closed position illustrated in FIG. 10 to an opened position when the arrangement 90c slides over rails 132 and 134 into position overlying opening 32c. The shelf and hood arrangement 90c is similar to the arrangement 90 illustrated in FIG. 7 and includes the pivoted shelf and detenting system. Consequently, it will be appreciated that as the arrangement 90c is displaced along rails 132 and 134, the door is moved from the closed to the opened position, enabling medical waste material to be passed through the entry slot of arrangement 90c into the container. The arrangement 90c can be removed from the container when the container is full of medical waste material and applied to an additional empty container.

It will also be appreciated from a review of FIGS. 7 and 10 that the container may be used without the hood and shelf arrangements 90. For example, in certain situations as in an operating room, it is not necessary to put on a hood and self arrangement with a restricted opening. Consequently, after the waste material has been deposited in the container, the handle on the doors may be used to close the container opening. Alternatively, of course, after such usage, the hood and shelf arrangement 90 may be applied to the lid of the container in the event that the medical waste material does not fill the container completely.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A container for hazardous medical waste material comprising:
   a container body including a plurality of walls;
   a cover for said container body, said cover defining an opening for receiving the waste material for disposition within the container body and having a ramp underlying said opening and extending into said container body for receiving waste material;
   a lid attached to said cover for movement between first and second positions, said lid in said first position overlying at least a major portion of said opening and having an edge defining with said cover an entry slot of predetermined size adjacent said ramp and through which said waste material is received for movement along said ramp into said container body;
   said lid being movable from said first position into said second position closing said opening and having at least one element engageable with said container body for securing said lid in said second position closing the container;
   said container body being formed of fiberboard and including a waterproof lining along one of interior and exterior surfaces of said container body.

2. A container according to claim 1 wherein said ramp terminates in an edge spaced from said cover and defines therewith an aperture through which waste material sliding along the ramp passes for disposition into said container body.

3. A container according to claim 1 wherein said one element includes a tab and said cover includes a slot for receiving the tab in the second position of said lid thereby to secure said lid to said cover in a position closing said opening.

4. A container for hazardous medical waste material comprising:
   a container body including a plurality of walls;
   a cover for said container body, said cover defining an opening for receiving the waste material for disposition within the container body and having a ramp underlying said opening and extending into said container body for receiving waste material;

a lid attached to said cover for movement between first and second positions, said lid in said first position overlying at least a major portion of said opening and having an edge defining with said cover an entry slot of predetermined size adjacent said ramp and through which said waste material is received for movement along said ramp into said container body;

said lid being movable from said first position into said second position closing said opening and having at least one element engageable with said container body for securing said lid in said second position closing the container;

said lid including a first hinge for pivoting said lid between said first and second positions, a second hinge spaced from said first hinge and said edge of said lid, a first lid portion extending between said first and second hinges and a second lid portion extending between said second hinge and said edge, said first lid portion forming an included acute angle with said cover and said second lid portion forming an included obtuse angle with said first lid portion in said first position of said lid, said first and second lid portions lying generally in a common plane with one another and with said cover when said lid lies in said second position thereof.

5. A container according to claim 4 wherein said one element includes a tab and said cover includes a slot for receiving the tab in the second position of said lid thereby to secure said lid to said cover, said tab and said slot having cooperable locking elements for securing said lid parallel to said cover in said second position of said lid.

6. A container for hazardous medical waste material comprising:

a container body including a plurality of walls;

a cover for said container body, said cover defining an opening for receiving the waste material for disposition within the container body and having a ramp underlying said opening and extending into said container body for receiving waste material;

a lid attached to said cover for movement between first and second positions, said lid in said first position overlying at least a major portion of said opening and having an edge defining with said cover an entry slot of predetermined size adjacent said ramp and through which said waste material is received for movement along said ramp into said container body;

said lid being movable from said first position into said second position closing said opening and having at least one element engageable with said container body for securing said lid in said second position closing the container;

said container body being formed of fiberboard, said fiberboard having a material applied thereto which changes color responsive to contact with liquid within said container.

7. A container for hazardous medical waste material comprising:

a container body including a plurality of walls;

a cover for said container body, said cover defining an opening for receiving the waste material for disposition within the container body and having a ramp underlying said opening and extending into said container body for receiving waste material;

a lid attached to said cover for movement between first and second positions, said lid in said first position overlying at least a major portion of said opening and having an edge defining with said cover an entry slot of predetermined size adjacent said ramp and through which said waste material is received for movement along said ramp into said container body;

said lid being movable from said first position into said second position closing said opening and having at least one element engageable with said container body for securing said lid in said second position closing the container;

said cover for said container body having dependent margins for disposition about said container body, and adhesive securing said cover and said container body to one another.

8. A container for hazardous medical waste material comprising:

a container body including a plurality of walls;

a cover for said container body, said cover defining an opening for receiving the waste material for disposition within the container body and having a ramp underlying said opening and extending into said container body for receiving waste material;

a lid attached to said cover for movement between first and second positions, said lid in said first position overlying at least a major portion of said opening and having an edge defining with said cover an entry slot of predetermined size adjacent said ramp and through which said waste material is received for movement along said ramp into said container body;

said lid being movable from said first position into said second position closing said opening and having at least one element engageable with said container body for securing said lid in said second position closing the container;

said ramp being pivotally connected to said cover adjacent one end of said ramp, said lid being coupled to said ramp to pivot said ramp toward a position closing said opening in response to pivotal movement of said lid in a direction tending to enlarge the size of said entry slot.

9. A container for supplying medical products and disposing of medical waste material comprising:

a container body including a plurality of walls for confining a supply of the medical products;

a cover for closing said container body when said container body contains the medical products;

an adhesive on one of said container body and said cover ineffective to secure the container body and said cover to one another when said container is used for supplying the medical products and effective to secure said container body and said cover to one another when said container is used for disposing medical waste;

said cover defining an opening for receiving the waste material when said container is used as a waste material container, said cover including an inclined surface underlying said opening and extending into said container body for receiving waste material;

a lid carried by said cover for movement between first and second positions, said lid in said first position overlying at least a major portion of said opening and having an edge defining with said cover an entry slot of predetermined size adjacent said inclined surface through which said waste material is received for sliding movement along said surface into said container body;

said lid being movable from said first position into said second position closing said opening and having at least one element engageable with said cover for securing said lid in said second position closing the opening through said cover whereby the medical waste material within the container body is sealed by said cover.

10. A container according to claim 9 wherein said inclined surface terminates in an edge spaced from said cover and defines therewith an aperture through which waste material slidable along the inclined surface passes for disposition into said container body.

11. A container according to claim 9 wherein said one element includes a tab and said cover includes a slot for receiving the tab in the second position of said lid thereby to secure said lid to said cover in a position closing said opening.

12. A container according to claim 9 wherein said container body is formed of fiberboard and includes a waterproof lining along one of interior and exterior surfaces of said container body.

13. A container according to claim 9 wherein said lid includes a first hinge for pivoting said lid between said first and second positions, a second hinge spaced from said first hinge and said edge of said lid, a first lid portion extending between said first and second hinges and a second lid portion extending between said second hinge and said edge, said first lid portion forming an included acute angle with said cover and said second lid portion forming an included obtuse angle with said first lid portion in said first position of said lid, said first and second lid portions lying generally in a common plane with one another and with said cover when said lid lies in said second position thereof.

14. A container according to claim 9 wherein said container body is formed of fiberboard, said fiberboard having a material applied thereto which changes color responsive to contact with liquid within said container.

15. A container according to claim 9 wherein said inclined surface is pivotally connected to said cover adjacent one end of said inclined surface, said lid being coupled to said inclined surface to pivot said inclined surface toward a position closing said opening in response to pivotal movement of said lid in a direction tending to enlarge the size of said entry slot.

16. A container for hazardous medical waste material comprising:
a container body including a plurality of walls and a cover, said cover defining an opening for receiving the waste material for disposition within the container body;
a door attached to said cover for movement between open and closed positions;
a hood carried by said cover for movement relative to said cover between a first position out of registration with said opening and a second position in registration with and overlying said opening, said hood and said door being coupled to one another such that said door is movable from said open position to said closed position in response to movement of said hood from said second position to said first position;
said hood defining an entry slot of predetermined size through which waste material is received for disposal in said container body.

17. A container according to claim 16 wherein said hood and said door are coupled to one another such that said door is movable from closed position to said open position in response to movement of said hood from said first position to said second position.

18. A container according to claim 16 wherein said door is articulated.

19. A container according to claim 18 wherein said container body is formed of fiberboard and includes a waterproof lining along one of interior and exterior surfaces of said container body.

20. A container according to claim 18 wherein said container body is formed of fiberboard, said fiberboard having a material applied thereto which changes color responsive to contact with liquid within said container.

21. A container according to claim 18 wherein said cover for said container body has dependent margins for disposition about said container body, and adhesive securing said cover and said container body to one another.

22. A method of converting a medical products supply container to a medical waste materials container comprising the steps of:
providing a container body having a plurality of walls and a bottom wall and a cover having an opening and a closure member movable between closed and open positions;
supplying medical products in said container body;
closing said container body with said cover and with said closure member in a closed position;
transporting the medical products in said container to a user;
removing the medical products from said container body; and
converting the supply container to a medical waste container including by moving said closure member to an open position and in response thereto providing a restricted entry slot into said container body whereby a user's hand cannot pass through said slot to said opening into the container body and among medical waste materials disposed in said container.

23. A method according to claim 22 wherein said closure member includes a lid articulated about two spaced parallel axes, and causing articulation of said lid about said pair of parallel axes such that a free edge of said lid in part defines with said cover and said entry slot.

24. A method according to claim 23 including providing a hood for movement relative to said cover between a first position out of registration with said opening and a second position in registration with and overlying said opening, coupling said hood and said closure member to one another to move said closure member from said open position to said closed position in response to movement of said hood from said second position to said first position and providing said restricted entry slot in said hood.

25. A method according to claim 24 including coupling said hood and said closure member to one another to move said closure member from said closed position to said open position in response to movement of said hood from said first position to said second position.

26. A method according to claim 23 including locking said lid to said cover when said container body is substantially filled with the medical waste materials.

27. A method according to claim 22 wherein said cover is releasably secured to said container body when the medical products are supplied in the container and permanently securing said cover to said container body when the supply container is converted to the medical waste materials container.

28. A container for supplying medical products and disposing of medical waste material comprising:
a container body including a plurality of walls for confining a supply of the medical products;
a cover for closing said container body when said container body contains the medical products;

engageable members on said container body and said cover ineffective to secure the container body and said cover to one another when said container is used for supplying the medical products and engageable with one another to secure said container body and said cover to one another when said container is used for disposing medical waste;

said cover defining an opening for receiving the waste material when said container is used as a waste material container, said cover including a surface underlying said opening and extending into said container body for directing waste material into the container body;

a lid carried by said cover for movement between first and second positions, said lid in said first position overlying a portion of said opening and having an edge defining with said cover an entry slot of predetermined size adjacent said surface through which said waste material is received for slidable movement along said surface into said container body;

said lid being movable from said first position into said second position closing said opening and having at least one element engageable with said cover for securing said lid in said second position closing the opening through said cover whereby the medical waste material within the container body is sealed by said cover.

29. A container for hazardous medical waste material comprising:

a container body including a plurality of walls and a cover, said cover defining an opening for receiving the waste material for disposition within the container body;

a door attached to said cover for movement between open and closed positions;

a hood carried by said cover for movement relative to said cover between a first position out of registration with said opening and a second position in registration with and overlying said opening, said hood and said door being coupled to one another such that said door is movable from said closed position to said open position in response to movement of said hood from said first position to said second position;

said hood defining an entry slot of predetermined size through which waste material is receivable for disposal in said container body.

30. A container for hazardous medical waste material comprising:

a container body including a plurality of walls and a cover, said cover defining an opening for receiving the waste material for disposition within the container body;

a door attached to said cover for movement between open and closed positions;

a hood removably carried by said cover between a first position separable from said cover and a second position on said cover in registration with and overlying said opening, a handle carried by said door for manually moving the door from said closed position to said open position when said hood lies in said first position;

said hood in said second position defining an entry slot of predetermined size through which waste material is receivable through said opening for disposal in said container body.

31. A container according to claim 30 wherein said container body is formed of fiberboard and includes a waterproof lining along one of interior and exterior surfaces of said container body.

32. A container for supplying medical products and disposing of medical waste material comprising:

a container body including a plurality of walls for confining a supply of the medical products;

a cover for closing said container body when said container body contains the medical products;

engageable members on said container body and said cover ineffective to secure the container body and said cover to one another when said container is used for supplying the medical products and engageable with one another to secure said container body and said cover to one another when said container is used for disposing medical waste;

said cover defining an opening for receiving the waste material when said container is used as a waste material container;

a door carried by said cover for movement between open and closed positions;

a hood removably carried by said cover between a first position separable from said cover and a second position on said cover in registration with and overlying said opening, a handle carried by said door for manually moving the door from said closed position to said open position when said hood lies in said first position;

said hood in said second position defining an entry slot of predetermined size through which waste material is receivable through said opening for disposal in said container body.

33. A container according to claim 32 wherein said container body is formed of fiberboard and includes a waterproof lining along one of interior and exterior surfaces of said container body.

* * * * *